(12) United States Patent
Alarcon

(10) Patent No.: US 12,045,860 B2
(45) Date of Patent: Jul. 23, 2024

(54) DATA CONNECTION FOR AN ELECTRONIC SMOKING DEVICE

(71) Applicant: Fontem Holdings 1 B.V., Amsterdam (NL)

(72) Inventor: Ramon Alarcon, Los Gatos, CA (US)

(73) Assignee: Fontem Ventures B.V., Amsterdam (NL)

( * ) Notice: Subject to any disclaimer, the term of this patent is extended or adjusted under 35 U.S.C. 154(b) by 0 days.

(21) Appl. No.: 16/952,835

(22) Filed: Nov. 19, 2020

(65) Prior Publication Data

US 2021/0076747 A1 Mar. 18, 2021

Related U.S. Application Data

(63) Continuation of application No. 15/219,033, filed on Jul. 25, 2016, now abandoned.

(51) Int. Cl.

| | |
|---|---|
| *G06Q 30/0251* | (2023.01) |
| *A24F 40/10* | (2020.01) |
| *A24F 40/60* | (2020.01) |
| *A24F 40/65* | (2020.01) |
| *A61M 15/06* | (2006.01) |
| *G06F 8/65* | (2018.01) |
| *G06F 16/21* | (2019.01) |
| *G06F 16/22* | (2019.01) |

(Continued)

(52) U.S. Cl.
CPC ......... *G06Q 30/0269* (2013.01); *A24F 40/60* (2020.01); *A24F 40/65* (2020.01); *G06F 8/65* (2013.01); *G06F 16/211* (2019.01); *G06F 16/22* (2019.01); *H04L 67/306* (2013.01); *A24F 40/10* (2020.01); *A61M 15/06* (2013.01); *H04W 8/22* (2013.01); *H04W 8/245* (2013.01)

(58) Field of Classification Search
CPC ........ A24F 40/60; G06F 16/22; G06F 16/211; G06F 8/65; H04L 67/306; G06Q 30/0269; H04W 8/22; H04W 8/245; A61M 15/06
See application file for complete search history.

(56) References Cited

U.S. PATENT DOCUMENTS

| | | | | |
|---|---|---|---|---|
| 9,877,505 | B2* | 1/2018 | Cameron | ................ A24F 40/05 |
| 9,888,724 | B2* | 2/2018 | Cameron | ............. H05B 47/105 |

(Continued)

FOREIGN PATENT DOCUMENTS

| | | |
|---|---|---|
| CN | 203262287 U | 11/2013 |
| CN | 203353682 U | 12/2013 |

(Continued)

OTHER PUBLICATIONS

Tsoi et al., "A Data Capturing Platform in the Cloud for Behavioral Analysis Among Smokers", 2015, IEEE (Year: 2015).*

(Continued)

*Primary Examiner* — Wei Y Zhen
*Assistant Examiner* — Junchun Wu
(74) *Attorney, Agent, or Firm* — Dykema Gossett PLLC

(57) ABSTRACT

A data exchange system comprises an electronic smoking device that includes identifying data and a database configured to i) receive the identifying data from the electronic smoking device, ii) receive user data for a user of the electronic smoking device from a processor, iii) associate the identifying data with user data to generate a user record, and iv) store the user record.

17 Claims, 2 Drawing Sheets

(51) Int. Cl.
*H04L 67/306* (2022.01)
*H04W 8/22* (2009.01)
*H04W 8/24* (2009.01)

(56) References Cited

U.S. PATENT DOCUMENTS

| | | | |
|---|---|---|---|
| 10,039,325 B2* | 8/2018 | Cameron | G08B 3/10 |
| 10,131,532 B2* | 11/2018 | Murison | F04B 19/006 |
| 10,617,150 B2* | 4/2020 | Cameron | A61M 11/042 |
| 11,083,228 B2* | 8/2021 | Memari | G01F 23/00 |
| 2008/0052698 A1 | 2/2008 | Olson et al. | |
| 2011/0125601 A1* | 5/2011 | Carpenter | G06Q 30/0631 |
| | | | 705/26.1 |
| 2011/0277764 A1 | 11/2011 | Terry et al. | |
| 2013/0284192 A1 | 10/2013 | Peleg et al. | |
| 2014/0107815 A1 | 4/2014 | LaMothe | |
| 2014/0173049 A1* | 6/2014 | Baker | H04L 67/51 |
| | | | 709/219 |
| 2015/0100441 A1* | 4/2015 | Alarcon | G06Q 20/20 |
| | | | 705/16 |
| 2015/0142387 A1* | 5/2015 | Alarcon | A61M 15/0083 |
| | | | 702/187 |
| 2015/0269628 A1* | 9/2015 | Urtso | G06Q 30/0269 |
| | | | 705/14.66 |
| 2016/0080469 A1* | 3/2016 | Liu | H04W 12/08 |
| | | | 709/219 |
| 2016/0143361 A1* | 5/2016 | Juster | A24F 40/65 |
| | | | 392/404 |
| 2016/0192712 A1* | 7/2016 | Memari | A24F 40/95 |
| | | | 141/2 |
| 2016/0211693 A1* | 7/2016 | Stevens | A24F 40/53 |
| 2016/0331029 A1* | 11/2016 | Contreras | A24F 40/50 |
| 2016/0374390 A1 | 12/2016 | Liu | |
| 2017/0048691 A1 | 2/2017 | Liu | |
| 2017/0064997 A1* | 3/2017 | Murison | A24F 40/53 |
| 2017/0118292 A1* | 4/2017 | Xiang | H04L 67/12 |
| 2017/0136301 A1* | 5/2017 | Cameron | A24F 40/65 |
| 2018/0286207 A1* | 10/2018 | Baker | A24F 40/65 |
| 2018/0303169 A1* | 10/2018 | Sears | A24F 40/60 |
| 2020/0250629 A1* | 8/2020 | Fernando | G07F 9/002 |
| 2021/0012400 A1* | 1/2021 | Locke | G06K 7/1417 |
| 2021/0308392 A1* | 10/2021 | Alarcon | A61M 11/042 |

FOREIGN PATENT DOCUMENTS

| | | | | |
|---|---|---|---|---|
| CN | 103653261 A | 3/2014 | | |
| CN | 104095299 A | 10/2014 | | |
| CN | 104980284 A | 10/2015 | | |
| CN | 105011373 A | 11/2015 | | |
| CN | 105722413 A | 6/2016 | | |
| EP | 2562967 A2 | 2/2013 | | |
| EP | 2862457 A1 | 4/2015 | | |
| EP | 3142506 B1 * | 12/2018 | | A24F 15/18 |
| ES | 2751059 T3 * | 3/2020 | | A24F 40/10 |
| RU | 2707892 C2 * | 12/2019 | | A24B 15/167 |
| WO | 2014199233 A2 | 12/2014 | | |
| WO | 2015120124 A1 | 8/2015 | | |

OTHER PUBLICATIONS

Robinson et al., "Electronic Cigarette Topography in the Natural Environment", Jun. 2015, PLOS one (Year: 2015).*

Etter, "Electronic cigarettes: a survey of users", 2010, BMC Public Health (Year: 2010).*

Behar et al., "Puffing Topography and Nicotine Intake of Electronic Cigarette Users", Feb. 2015, PLOS one (Year: 2015).*

* cited by examiner

DATA CONNECTION FOR AN ELECTRONIC SMOKING DEVICE

CROSS-REFERENCE TO RELATED APPLICATIONS

This application is a continuation of U.S. application Ser. No. 15/219,033, filed 25 Jul. 2016 (the '033 application). The '033 application is hereby incorporated by reference as though fully set forth herein.

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g., a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an airflow pattern through the device). The airflow sensor indicates or signals the puff to the control electronics to power up the device and generate vapor. In other e-cigarettes, a switch is used to power up the e-cigarette to generate a puff of vapor.

SUMMARY OF THE INVENTION

In accordance with one aspect of the present invention there is provided a data exchange system for an electronic smoking device. The system comprises the electronic smoking device comprising identifying data. The system also comprises a database configured to i) receive the identifying data from the electronic smoking device, ii) receive user data for a user of the electronic smoking device from a processor, iii) associate the identifying data with user data to generate a user record, and iv) store the user record.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, the same element numbers indicate the same elements in each of the views.

DESCRIPTION OF THE PREFERRED EMBODIMENTS

Figure 1:
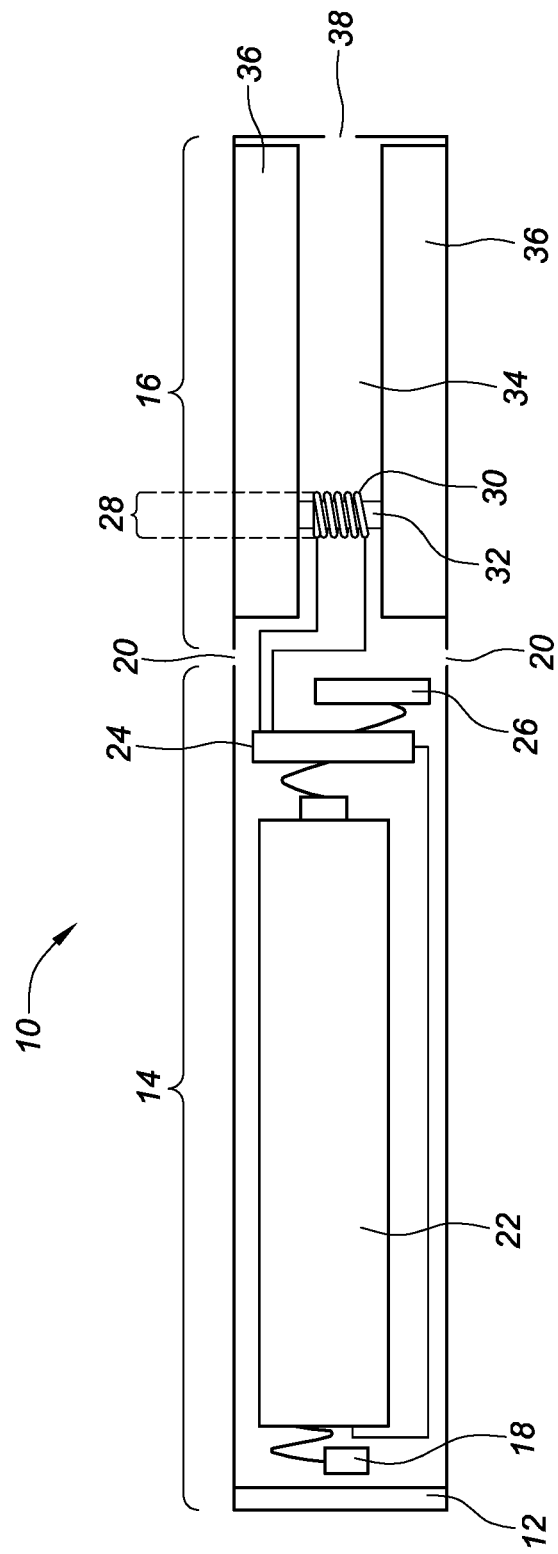
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette (or eCig) 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
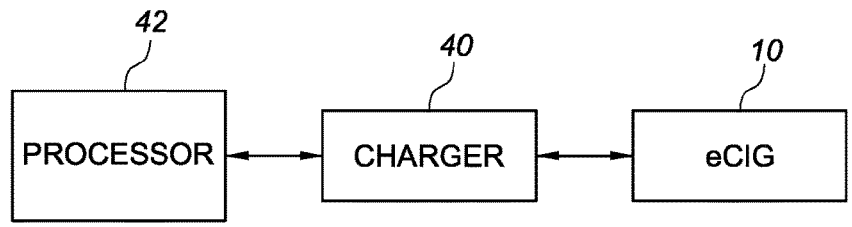
FIG. 2 is a block diagram illustrating data communication pathways between an exemplary e-cigarette and a processor.

FIG. 2 is a block diagram depicting data exchange pathways between the e-cigarette 10, a charger 40, and a processor 42. The e-cigarette 10 can connect to a charger 40 in order to charge the battery 22 (see FIG. 1) of the e-cigarette 10. In addition to this charging function, the charger 40 can exchange data with the e-cigarette 10. The data exchange can occur, for example, through a dedicated data line or signals obtained from a power line connecting the charger 40 and the e-cigarette 10 during charging. When a data line is used to transfer data between the e-cigarette 10 and the charger 40, the data line can be a physical wire connection or a wireless communication. In an embodiment, the data that can be transferred from the e-cigarette 10 to the charger 40 includes identifying data, such as a serial number, a calibration parameter, a batch code, a line number, or a barcode associated with the e-cigarette 10. In another embodiment, the data that can be transferred from the e-cigarette 10 to the charger 40 includes usage data, such as a number of puffs taken, an average length of puffs taken, a smoke juice level, a smoke juice flavor, or a location of use.

The charger 40 can also exchange data with the processor 42, such as through a dedicated data line or power line as described above. In an embodiment, the processor 42 can be a personal computer (PC), a tablet PC, or a mobile device, such as a smart phone. In another embodiment, the processor 42 can be a charging or holding pack for the e-cigarette 10. The processor 42 may have a custom communication driver (e.g., an application) that enables it to exchange data with the charger 40. The data that can be transferred from the charger 40 to the processor 42 includes identifying and usage data from the e-cigarette 10, for example, as described above. In an embodiment, data can also be transferred from the processor 42 to the charger 40, including data related to various charging protocols, for example.

Figure 3:
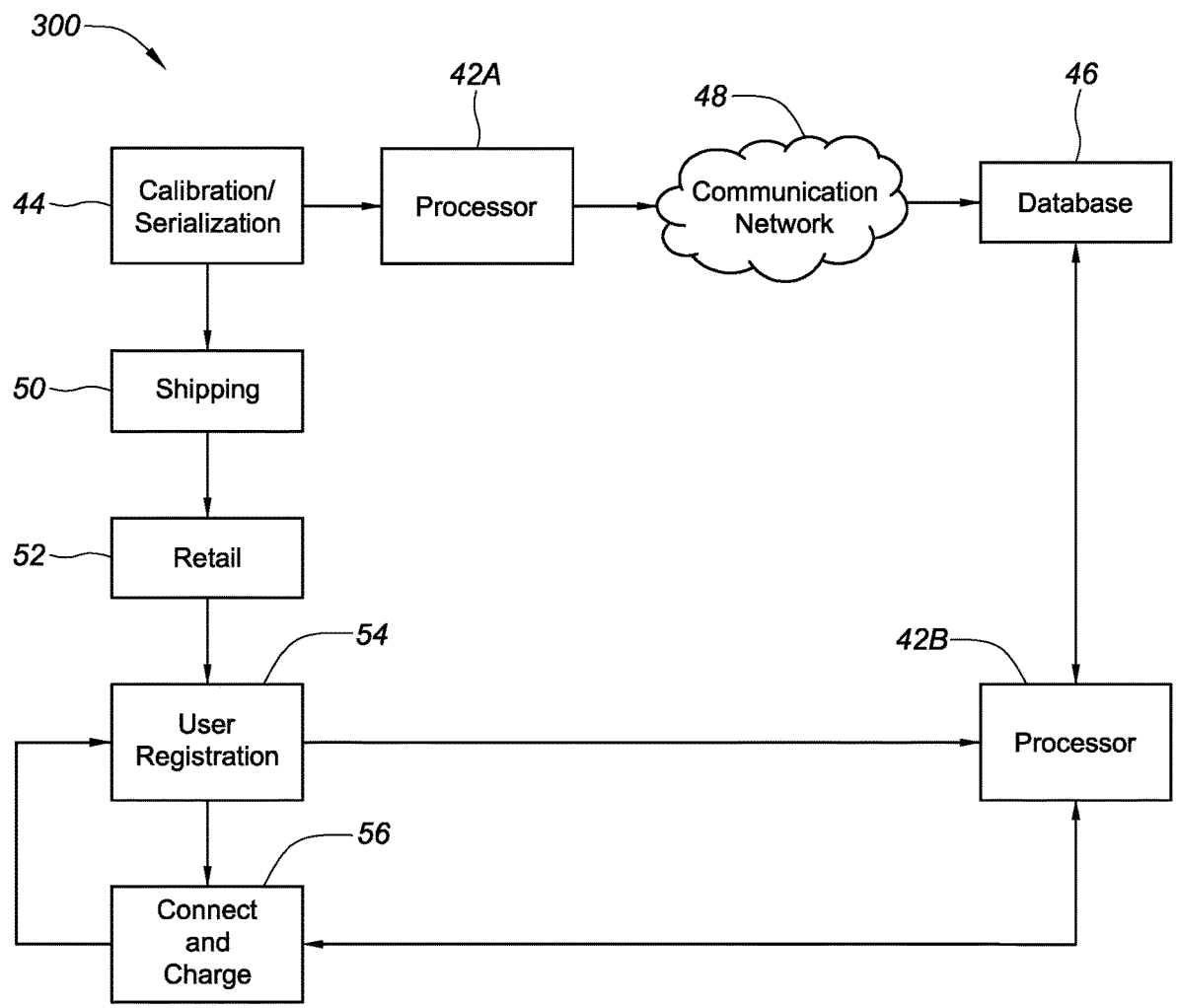
FIG. 3 is a block diagram illustrating an exemplary data exchange system.

FIG. 3 is a block diagram illustrating an exemplary data exchange system 300. At step 44, calibration and/or serialization of the e-cigarette 10 occurs. This step typically takes place at a factory or manufacturing facility. The e-cigarette can be calibrated according to various factors. For example, in a system using a flow sensor, in order to ensure that the output of the flow sensor is accurate, the manufacturing system may present one or more known reference flows to the e-cigarette during the calibration procedure. The flow sensor can then calibrate its signal to the reference flow using offset and/or multiplying factors. Another calibration may be for voltage measurement purposes. The manufacturing system can present a known reference voltage, and the e-cigarette can then compare its voltage reading to the known reference and produce an offset so that it reports the same voltage level as the reference. In the above two cases, the calibration can either be done by a processor and then the calibration parameters can be sent to the e-cigarette, or the calibration can be done by the e-cigarette itself. In addition to or instead of calibration, the e-cigarette can be assigned a serial number or other identifying label, such as a batch code, a date of production, a line number, or a barcode.

Once the calibration/serialization step 44 has occurred, the identifying data associated with the e-cigarette 10 can be transferred to a database 46 for storage and processing. The database 46 can be a manufacturing database, which may also include marketing information or link to a separate database with marketing information. Identifying data from the e-cigarette 10 can be transferred to the database 46 via a processor 42A. Identifying data from the e-cigarette 10 can be transferred to the processor 42A either directly (e.g., via a wireless connection, such as Bluetooth, between the e-cigarette 10 and the processor 42A) or via a charger, such as described above with respect to FIG. 2. The processor 42A can then transfer the data to the database 46 either directly or via a communication network 48, such as a server-based network, LAN, WAN, Internet, intranet, Wi-Fi network, Bluetooth network, cellular network and/or the like.

Subsequent to the calibration/serialization step 44 and the transfer of identifying data to the database 46, the e-cigarette is shipped at step 50 and sold in a retail setting, such as a store, kiosk, or online retailer, at step 52. After purchase, a user may register the e-cigarette 10 during a user registration step 54. The user may register the e-cigarette by using a processor 42B, for example. In addition, a communication network (not shown in FIG. 3) may be used in the process of registration.

During the user registration step 54, the user may enter demographic data (e.g., name, age, gender, location, hobbies, flavor preferences, etc.) as well as the identifying data from the purchased e-cigarette 10 into the processor 42B. The processor 42B can then communicate this information to the database 46 either directly or via a communication network (not shown in FIG. 3).

Next, the user will eventually connect the registered e-cigarette 10 to a charger at step 56. While the e-cigarette 10 is charging, usage data can be transferred from the charger to the processor 42B, as described above with respect to FIG. 2. In some embodiments, the e-cigarette may be connected directly to the processor 42B without using the charger as an intermediary.

In an embodiment, usage data can include a number of puffs taken, an average length of puffs taken, a smoke juice level, a smoke juice flavour, or a location of use of the e-cigarette 10. Once the usage data has been transferred to the processor 42B, it can subsequently be transferred to the database 46. The database 46 can then associate the user data (including demographic and usage data) with the identifying data for a given e-cigarette 10, thereby creating a user record. The database 46 can store multiple user records.

User records stored within the database 46 can be used for several purposes. In an embodiment, user records can be used to provide firmware updates to the user for their e-cigarette 10. If a user record indicates that a particular device requires a firmware update (e.g., based on date of purchase, level of use, location of use, and/or the like), the database 46 can provide the firmware update to the processor 42B. The processor 42B may have an application (i.e., an "app") enabling it to receive and communicate the firmware update. When the user connects their e-cigarette 10 to the processor 42B (either directly or via a charger), the firmware can be updated. Alternatively, a user can obtain a firmware update for their e-cigarette 10 by requesting it directly from a processor or communication network (e.g. the manufacturer's website) that can communicate with the database 46.

Other uses of user records stored within the database 46 include tracing a given device, providing customer support, preventing piracy related to the sale of electronic smoking devices, and providing marketing information or opportunities. In an embodiment, the database 46 can use user records to provide a coupon, a rebate, an offer, a deal, a name of a vendor, a location of a vendor, an inventory of a vendor, an electronic purchase order, or an electronic payment. This marketing information can be provided to the user via the processor 42B, for example.

In summary, in one aspect a data exchange system for an electronic smoking device is provided, the data exchange system comprising the electronic smoking device comprising identifying data; and a database configured to i) receive the identifying data from the electronic smoking device, ii) receive user data for a user of the electronic smoking device from a processor, iii) associate the identifying data with user data to generate a user record, and iv) store the user record.

In one aspect, the electronic smoking device comprises firmware; wherein the database is further configured to provide a firmware update to the processor based on the user record; and wherein the processor is further configured to transmit the firmware update to the electronic smoking device.

In one aspect, the database is further configured to provide marketing information to the processor based on the user record.

The marketing information may comprise at least one of the following: a coupon, a rebate, an advertisement, an offer, a deal, a name of a vendor, a location of the vendor, an inventory of the vendor, an electronic purchase order, or an electronic payment.

In one aspect, the identifying data comprises at least one of a serial number, a calibration parameter, a batch code, a date, a line number, or a barcode.

In one aspect, the user data comprises at least one of a user demographic, a number of puffs taken on the electronic smoking device, an average length of puffs taken on the electronic smoking device, a smoke juice level of the electronic smoking device, a smoke juice flavour used in the electronic smoking device, or a location of the electronic smoking device.

In one aspect, the processor comprises at least one of a personal computer or a mobile device.

In one aspect, the database is configured to receive the identifying data or the user data via a communication network.

In one aspect, the processor is configured to receive the user data from the electronic smoking device via a charger.

In one aspect, the database is configured to receive the identifying data from the electronic smoking device via a processor.

Further provided is a method for providing a firmware update to an electronic smoking device, the method comprising: assigning identifying data to the electronic smoking device; collecting user data for a user of the electronic smoking device; associating the identifying data with the user data to generate a user record; providing the firmware update based on the user record.

In one aspect, the identifying data comprises at least one of a serial number, a calibration parameter, a batch code, a date, a line number, or a barcode.

In one aspect, the user data comprises at least one of a user demographic, a number of puffs taken on the electronic smoking device, an average length of puffs taken on the electronic smoking device, a smoke juice level of the electronic smoking device, a smoke juice flavour used in the electronic smoking device, or a location of the electronic smoking device.

In one aspect, providing the firmware update to the electronic smoking device comprises transmitting the firmware update to a processor configured to communicate with the electronic smoking device.

In one aspect, the processor comprises a personal computer or a mobile device.

Further provided is a method for generating a user record associated with a user of an electronic smoking device, the method comprising: assigning identifying data to the electronic smoking device; collecting user data for a user of the electronic smoking device; and associating the identifying data with the user data to generate a user record.

In one aspect, the identifying data comprises at least one of a serial number, a calibration parameter, a batch code, a date, a line number, or a barcode.

In one aspect, the user data comprises at least one of a user demographic, a number of puffs taken on the electronic smoking device, an average length of puffs taken on the electronic smoking device, a smoke juice level of the electronic smoking device, a smoke juice flavour used in the electronic smoking device, or a location of the electronic smoking device.

In one aspect, the method further comprises tracing the electronic smoking device using the user record.

In one aspect, the method further comprises providing marketing information to the user based on the user record.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 electronic smoking device
12 end cap
14 power supply portion
16 atomizer/liquid reservoir portion
18 light-emitting diode (LED)
20 air inlets
22 battery
24 control electronics
26 airflow sensor
28 atomizer
30 heating coil
32 wick
34 central passage
36 liquid reservoir
38 air inhalation port
40 charger
42/42A/42B processor
44 calibration/serialization step
46 database
48 communication network
50 shipping step
52 retail step
54 user registration step
56 connect and charge step

The invention claimed is:

1. A data exchange system for an electronic smoking device, the system comprising:
the electronic smoking device comprising identifying data comprising a serial number that has been assigned to the electronic smoking device in a serialization step and configured to transfer the identifying data to a first processor directly or via a charger of the electronic smoking device, wherein the electronic smoking device comprises firmware; and
a database configured to:
i) receive the assigned identifying data via a first processor,
ii) receive the identifying data of the electronic smoking device and demographic data of a user of the electronic smoking device via a second processor for registering the electronic smoking device,
iii) receive usage data for the user from the registered electronic smoking device via the second processor, wherein the usage data comprises at least one of a smoke juice level of the electronic smoking device and a smoke juice flavor, and
iv) associate the identifying data with the demographic data and the usage data to generate a user record,
v) store the user record,
vi) trace the electronic smoking device over time using the stored user record, and
vii) determine a firmware update is required for the electronic smoking device based on the user record and a date of purchase of the electronic smoking device, wherein the firmware update is provided by the database to the second processor, wherein the second processor is further configured to transmit the firmware update to the electronic smoking device;
wherein the electronic smoking device is configured to be physically separate from, and not directly connectable via a wired connection to, the first processor and the second processor.

2. The data exchange system of claim 1, wherein the database is further configured to provide marketing information to the second processor based on the user record.

3. The data exchange system of claim 2, wherein the marketing information comprises at least one of the following: a coupon, a rebate, an advertisement, an offer, a deal, a name of a vendor, a location of the vendor, an inventory of the vendor, an electronic purchase order, or an electronic payment.

4. The data exchange system of claim 1, wherein the identifying data further comprises at least one of a calibration parameter, a batch code, a date, a line number, or a barcode.

5. The data exchange system of claim 1, wherein the usage data further comprises at least one of a number of puffs taken on the electronic smoking device, an average length of puffs taken on the electronic smoking device, or a location of the electronic smoking device.

6. The data exchange system of claim 1, wherein at least one of the first processor and the second processor comprises at least one of a personal computer or a mobile device.

7. The data exchange system of claim 1, wherein the database is configured to receive the identifying data or the user data via a communication network.

8. The data exchange system of claim 1, wherein the second processor is configured to receive the usage data from the electronic smoking device via a charger.

9. The data exchange system of claim 1, wherein the database is further configured to provide marketing information comprising at least one of a location of a vendor or an inventory of the vendor to the second processor based on the user record.

10. The data exchange system of claim 5, wherein the electronic smoking device further comprises an airflow sensor, and wherein the airflow sensor is configured to act as a puff detector.

11. A method for generating a user record associated with a user of an electronic smoking device, the method comprising:
   assigning identifying data comprising a serial number to the electronic smoking device in a serialization step, transferring the identifying data to a first processor directly or via a charger of the electronic smoking device, and providing the assigned identifying data to a database via the first processor;
   registering the electronic smoking device with the database by transmitting, the identifying data of the electronic smoking device and demographic data of a user of the electronic smoking device to the database via a second processor;
   collecting usage data for the user by the registered electronic smoking device, wherein the usage data comprises at least one of a smoke juice level of the electronic smoking device and a smoke juice flavor, and transmitting the usage data to the database via the second processor;
   associating the identifying data with the demographic data and the usage data by the database to generate a user record;
   tracing the electronic smoking device over time using the stored user record;
   determining a firmware update is required for the electronic smoking device based on the user record and a date of purchase of the electronic smoking device, wherein the electronic smoking device comprises firmware; and
   providing the firmware update to the electronic smoking device by transmitting the firmware update to the second processor configured to communicate with the electronic smoking device;
   wherein the electronic smoking device is configured to be physically separate from, and not directly connectable via a wired connection to, the first processor and the second processor.

12. The method of claim 11, wherein the identifying data further comprises at least one of a calibration parameter, a batch code, a date, a line number, or a barcode.

13. The method of claim 11, wherein the usage data further comprises at least one of a number of puffs taken on the electronic smoking device, an average length of puffs taken on the electronic smoking device, or a location of the electronic smoking device.

14. The method of claim 11, wherein at least one of the first processor and the second processor comprises a personal computer or a mobile device.

15. The method of claim 11, further comprising the step of: tracing the electronic smoking device using the user record.

16. The method of claim 11, further comprising the step of: providing marketing information to the user based on the user record.

17. The method of claim 16, wherein the marketing information comprises comprising at least one of a location of a vendor or an inventory of the vendor to the second processor based on the user record.

* * * * *